(12) United States Patent
Meehan

(10) Patent No.: US 7,700,083 B2
(45) Date of Patent: Apr. 20, 2010

(54) SKIN CARE COMPOSITION FOR ACCELERATED PRODUCTION OF COLLAGEN PROTEINS AND METHOD OF FABRICATING SAME

(76) Inventor: Kevin Meehan, P.O. Box 4616, Jackson, WY (US) 83001

( * ) Notice: Subject to any disclaimer, the term of this patent is extended or adjusted under 35 U.S.C. 154(b) by 224 days.

(21) Appl. No.: 11/462,347

(22) Filed: Aug. 3, 2006

(65) Prior Publication Data

US 2007/0092472 A1    Apr. 26, 2007

Related U.S. Application Data

(60) Provisional application No. 60/729,880, filed on Oct. 24, 2005.

(51) Int. Cl.
| A61K 38/39 | (2006.01) |
| A61K 31/716 | (2006.01) |
| A61K 33/34 | (2006.01) |
| A61K 8/65 | (2006.01) |
| A61K 31/315 | (2006.01) |

(52) U.S. Cl. .............. 424/70.14; 424/638; 514/12; 514/54; 514/494; 562/433

(58) Field of Classification Search ............ 514/12, 514/54, 494; 424/70.14, 638; 436/90; 562/433
See application file for complete search history.

(56) References Cited

U.S. PATENT DOCUMENTS

| 3,891,765 | A | 6/1975 | Coirre et al. |
| 3,932,638 | A | 1/1976 | Coirre et al. |
| 4,414,202 | A | 11/1983 | Silvetti |
| 4,424,232 | A | 1/1984 | Parkinson |
| 4,711,780 | A | 12/1987 | Fahim |
| 4,778,679 | A | 10/1988 | Silvetti |
| 5,198,465 | A | 3/1993 | Dioguardi |
| 5,656,608 | A | 8/1997 | Schneider et al. |
| 5,733,884 | A | 3/1998 | Barbul et al. |
| 5,827,874 | A | 10/1998 | Meyer et al. |
| 5,858,993 | A | 1/1999 | Pickart |
| 5,922,346 | A * | 7/1999 | Hersh .................. 424/439 |
| 6,048,543 | A | 4/2000 | Schneider et al. |
| 6,103,748 | A * | 8/2000 | Bryan .................. 514/400 |
| 6,358,539 | B1 | 3/2002 | Murad |
| 6,676,977 | B2 | 1/2004 | Murad |
| 6,686,340 | B2 | 2/2004 | Rath |
| 6,919,071 | B2 | 7/2005 | Choulot et al. |
| 2002/0013359 | A1 | 1/2002 | Dioguardi |
| 2003/0203008 | A1 | 10/2003 | Gunasekaran |
| 2004/0081681 | A1 | 4/2004 | Vromen |
| 2004/0131648 | A1 | 7/2004 | deLong et al. |
| 2004/0247633 | A1 | 12/2004 | Eberl et al. |
| 2004/0265268 | A1 * | 12/2004 | Jain .................. 424/85.1 |
| 2005/0129787 | A1 | 6/2005 | Murad |
| 2005/0209130 | A1 | 9/2005 | Patt |

OTHER PUBLICATIONS

Collagenics- Product Catalog of Metagenics, 2 pages (Aug. 23, 2006).*

* cited by examiner

*Primary Examiner*—Chih-Min Kam
(74) *Attorney, Agent, or Firm*—Marger Johnson & McCollom PC

(57) ABSTRACT

A liquid solution for topical application to the skin of an animal consists of solutes and a solvent, where the solutes include ascorbate, tropocollagen factors, copper, and zinc gluconate. The tropocollagen factors include L-proline, glycine and L-lysine.

25 Claims, No Drawings

SKIN CARE COMPOSITION FOR ACCELERATED PRODUCTION OF COLLAGEN PROTEINS AND METHOD OF FABRICATING SAME

CROSS REFERENCE TO RELATED APPLICATIONS

This application claims the benefit of U.S. Provisional Application No. 60/729,880, which was filed on 24 Oct. 2005. U.S. Provisional Application No. 60/729,880 is incorporated by reference in its entirety.

BACKGROUND

1. Technical Field

This disclosure relates generally to a topical skin care composition, and more specifically to a topical skin care composition formulated to provide accelerated production of collagen proteins.

2. Description of the Related Art

Collagen is one of the long, fibrous structural proteins whose functions are quite different from those of globular proteins such as enzymes. Collagen is the main protein of connective tissue in animals and the most abundant protein in mammals, making up about 40% of the total. It is tough and inextensible, with great tensile strength, and is the main component of cartilage, ligaments and tendons, and the main protein component of bone and teeth. Along with soft keratin, it is responsible for skin strength and elasticity, and its degradation leads to wrinkles that accompany aging. Collagen strengthens blood vessels and plays a role in tissue development. Collagen is present in the cornea and lens of the eye in crystalline form. It is also used in cosmetic surgery and burn surgery.

Collagen occurs in many places throughout the body, and in many different forms, each form being known as a type. There are at least 12 different types of collagen, with Type I collagen being the most abundant. The basic triple-helix structure of Type I collagen is the prototype for most of the other collagen types.

The other types of collagen differ from Type I collagen in the length of their triple helix and the presence or absence of globular domains at their amino or carboxyl terminal ends. Type I collagen may be found in skin, tendons, and bone, and Types I-III are recognized as playing a vital role in skin development and formation.

Collagen itself is made up of a unique Amino Acid (AA) and Imino Acid (IA) composition with 33% of the total residues being glycine (Gly), 10% proline (Pro), 10% hydroxyproline (Hyp), and about 1% hydroxylysine (Hyl).

The basic structural unit of Type I, II, and III collagen is tropocollagen, which is cross-linked to from large fibers of collagenous tissues. Tropocollagen is made of three polypeptide chains called α chains, where each of the α chains is wound around the other to form a triple helix structure. Every third AA or IA in the α chain is a glycine (hence the value of 33% for the relative amount of glycine present in collagen).

Sixty percent of the α chains are made of either the sequence Gly-Pro-X or the sequence Gly-X-Hyp, where X may be any AA or IA. The remaining forty percent of the α chains are various sequences of AAs and IAs, with every third AA or IA being a glycine. The AAs and IAs that compose tropocollagen may be referred to as tropocollagen factors.

A subset of particular proline and lysine residues in the region where the triple-helix formation occurs are hydroxylated before assembly can take place. Three enzymes are required for proper hydroxylation: lysl hydroxylase, prolyl-4-hydroxylase, and prolyl-3-hydroxylase.

Lysl hydroxylase converts lysines in the sequence X-Lys-Gly to 5-hydroxylysine. Prolyl-4-hydroxylase converts prolines in the sequence X-Pro-Gly to 4-hydroxyproline. Prolyl-3-hydroxylase converts prolines in the sequence Hyp-Pro-Gly to 3-hydroxyproline. The above hydroxylation reactions require $Fe^{2+}$, ascorbic acid (vitamin C), oxygen, and α-ketoglutarate in the chemical reaction that is described below in equation (1).

$$\text{AA or IA residue} + \text{ascorbic acid} + O_2 + \alpha\text{-ketoglutarate} \rightarrow \text{hydroxyl-AA or IA} + \text{succinate} \qquad (1)$$

Since the presence of new collagen proteins encourages the replication of skin cells, the topical application of tropocollagen factors has been used to treat skin conditions such as sun-burn, malasma, wrinkling, telangiectasias (spider-veins), and dilated pores.

However, as was explained above, in order to hydroxylate new collagen proteins in order to synthesize new Type I, II, and III collagen, the tropocollagen factors found in conventional topical products must react with the pre-existing ascorbic acid that is found in the body.

Embodiments of the invention address this and other disadvantages of the conventional art.

DETAILED DESCRIPTION OF EXAMPLE EMBODIMENTS

The inventor has recognized that the replication of new collagen proteins may be advantageously accelerated compared to conventional products by providing ascorbic acid (vitamin C) or a compound containing ascorbic acid, such as an ascorbate, and tropocollagen factors, such as proline, glycine, and lysine, in a skin care composition for topical application. Compared to conventional products that provide little or no additional ascorbic acid, the presence of the increased amounts of additional ascorbic acid encourages the accelerated production of collagen proteins (Types I, II, and III), and in turn, the increased replication of, among other things, skin cells.

The inventor has further recognized that the presence of a transitional metal, such as copper, in a topical product may advantageously contribute to the production of the pigment melanin.

The applicant has further recognized that the presence of zinc in a topical product containing a transitional metal such as copper synergistically provides maintenance of the integrity of biological membranes for protection against oxidative injury that might otherwise result from the elevated copper levels.

The above and other advantages associated with topical compositions according to embodiments of the invention are described in further detail below.

When expressing concentrations of a substance, the mass-volume percentage may be used for solutions made from solid reagents. For purposes of this disclosure, the mass-volume percentage, which is abbreviated as "% m/v," is defined as the mass of the solute in grams divided by the volume of solution in milliliters and multiplied by one hundred. The mass-volume percentage denotes the mass of the substance in a mixture as a percentage of the volume of the entire mixture.

Table I lists some ingredients included in topical compositions according to some preferred embodiments of the invention, as well as the preferred concentration ranges for those ingredients. In Table I, the concentration ranges for the ingredients are given in mass-volume percentage (% m/v).

TABLE I

| Component | concentration range, in % m/v |
|---|---|
| L-Ascorbate | from 15 to 30 |
| L-Proline | from 2 to 5 |
| Glycine | from 2 to 5 |
| L-Lysine | from .5 to 2 |
| Copper | from .5 to 5.0 |
| Bioflavonoids | from .5 to 1.5 |
| beta-1,3D-glucans | from .05 to .15 |
| Zinc gluconate | from .01 to .03 |
| Silicon | from .01 to .03 |

An exemplary topical skin care composition according to a preferred embodiment of the invention includes the solutes listed below in Table II. In Table II, the concentrations of the listed ingredients are given in mass-volume percentage. To obtain the topical skin care composition, which is a liquid solution, the solutes listed in Table II are blended in a solvent of 5% alcohol solution consisting of alcohol and distilled water.

It will be understood by those of skill in the art that the solvent need not be a 5% alcohol solution, other embodiments of the invention may utilize other suitable solvents. For example, the solvent may be pure distilled water, or a 3% alcohol solution, or a 7% alcohol solution.

TABLE II

| Component | concentration, in % m/v |
|---|---|
| L-Ascorbate | 21.5 |
| L-Proline | 3.33 |
| Glycine | 3.33 |
| L-Lysine | 1.31 |
| Copper | 1.0 |
| Bioflavonoids | 1.0 |
| Beta-1,3D-glucans | 0.10 |
| Zinc gluconate | 0.021 |
| Silicon | 0.02 |

According to alternative embodiments of the invention, a topical skin care product composition may include more or less ingredients than those listed above in Tables I and II. It will be understood by those of skill in the art that additional ingredients, such as fragrance or moisturizer, may be added to the ingredients listed in Tables I and II without departing from the teachings of the invention.

In the following paragraphs, some of the chemical properties and the advantageous contributions associated with the ingredients listed in Tables I and II are described.

As indicated in Tables I and II, topical compositions for accelerated production of collagen proteins according to some embodiments of the invention include ascorbate. In the preferred composition described in Table II, the ascorbate amounts to about 21.5% m/v of the composition.

Ascorbates are mineral salts of ascorbic acid, which is weakly acidic. Typically, ascorbates are powders that are manufactured by reacting ascorbic acid with mineral carbonates in aqueous solutions, venting the carbon dioxide, drying the reaction product, and then milling the dried product to the desired particle size. Some examples of mineral carbonates suitable for reaction with ascorbic acid to form ascorbates include calcium carbonate, potassium carbonate, sodium bicarbonate, and magnesium carbonate. According to embodiments of the invention, one ascorbate or several different ascorbates may be used in the topical composition.

Because ascorbates are dry solids, they may be easily stored and measured and this is one reason why they are preferred as ingredients for the embodiments specified in Tables I and II. It is understood that when the ascorbates are dissolved in solution, ascorbic acid is produced and may participate in the hydroxylation of tropocollagen factors as described in equation (1) above. In alternative embodiments of the invention, topical compositions may substitute ascorbic acid for the ascorbates or may use mixtures of both ascorbic acid and ascorbates.

As was explained above, ascorbic acid is critical to the hydroxylation of tropocollagen to form new collagen proteins. According to embodiments of the invention, compositions for topical application include significantly increased amounts of ascorbic acid or ascorbates compared to conventional formulations in order to obtain an improved composition for accelerated production of collagen proteins.

As indicated in Tables I and II, topical compositions for accelerated production of collagen proteins according to embodiments of the invention include glycine, L-lysine, and L-proline. In the preferred composition described in Table II, the glycine, lysine, and proline amount to about 3.33% m/v, 1.31% m/v, and 3.33% m/v, respectively.

Since glycine is the simplest AA in the body and is of major importance in the synthesis of proteins, the sequencing requirement of this substance for the alpha chains becomes readily apparent. In other words, the body's capability of synthesizing adequate amounts of glycine under stress loading may be of concern, particularly in the field of collagen protein generation.

The essential AA lysine participates in the biosynthesis of proteins and the residues that are not metabolized in the liver are transported to various tissues in the body, such as connective tissues and skin. As was described above, the unique AA and IA composition of collagen includes hydroxylysine (Hyl), which is a modified form of lysine. In order to produce 5-hydroxylysine (Hyl) from the lysine residues in the sequence X-Lys-Gly through a hydroxylation process, the enzyme lysyl hydroxylase is required.

The IA proline is synthesized from glutamate, and in the modified form is recognized as hydroxyproline which is found in structural proteins. Of interest here is its role in tropocollagen. When activated by the enzyme prolyl-4-hydroxylase, the prolines in the sequence X-Pro-Gly are converted to 4-hydroxyproline. The enzyme Prolyl-3-hydroxylase converts prolines in the sequence Hyp-Pro-Gly to 3-hydroxyproline.

All three of the above reactions require ascorbic acid for their hydroxylation reactions to occur, and the ascorbic acid is readily available because of the amount of ascorbate in the composition.

As indicated in Tables I and II, topical compositions for accelerated production of collagen proteins according to embodiments of the invention further include copper, which is a transitional metal. In the preferred composition described in Table II, the copper totals about 1.0% m/v of the composition.

The relationship of the transitional metal copper and its role in the biosynthesis of the biological pigments, such as melanin, is described in the following paragraphs.

Melanocytes depend on the enzyme tyrosinase to catalyze the subsequent reaction of tyrosine to dopa, which in turn initiates the synthesis of melanins. Copper is the required cofactor in this biosynthesis process.

However, the redox cycling between cuprous ($Cu^+$) and cupric ($Cu^{2++}$) ions can generate a highly reactive oxygen species that is destructive to biological membranes. Some intracellular proteins, such as metallothionein, have protecting mechanisms that safeguard against the potential toxicity of the copper ions. These protective intracellular proteins may be referred to as copper chaperones, since they have the ability to bind with copper ions, preventing them from generating the destructive oxygen species.

The inventor has recognized that increasing the amount of elemental copper to levels beyond what is typically found in topical skin care compositions beneficially increases the production of melanin. The inventor has further recognized that the potentially destructive presence of increased copper ions may be effectively counter-acted by increasing the copper chaperones that are present. The mechanism for achieving this will be explained in further detail below.

It should also be noted that the enzyme lysyl oxidase, which is necessary for the cross-linking of both collagen and elastin, requires copper for its proper function. For the above reasons, copper may be advantageously included in the embodiments described in Tables I and II.

As indicated in Tables I and II, topical compositions for accelerated production of collagen proteins according to embodiments of the invention further include bioflavonoid extracts. In the preferred composition described in Table II, the bioflavonoid extracts amount to about 1.0% m/v of the composition.

Bioflavonoid extracts demonstrate a wide range of pharmacological activities. In particular, one class of bioflavonoids, the proanthocyanidins (which include the extracts from pine bark and grape seed), are known for increasing intercellular vitamin C levels and inhibiting the destruction of collagen. Thus, bioflavonoids in general, and proanthocyanidins in particular, are well-suited for embodiments of the invention due to their beneficial interaction with ascorbic acid and collagen.

Additionally, the inventor has recognized that because bioflavonoids exhibit a cyto-protective effect that reduces inflammation and protects tissues, they can be used to reinforce the natural cross-linking that forms the collagen matrix. For this additional reason, bioflavonoid extracts are advantageously included in the embodiments of the invention described in Tables I and II.

As indicated in Tables I and II, topical compositions for accelerated production of collagen proteins according to embodiments of the invention further include beta-1,3D-glucans. In the preferred composition described in Table II, the beta-1,3D-glucans totals about 0.1% m/v of the composition.

Beta-D-glucans, usually referred to as beta-glucans, comprise a class of non-digestible polysaccharides widely found in nature in such sources as oats, barley, yeast, bacteria, algae and mushrooms. In oats, barley and other cereal grains, they are located primarily in the endosperm cell wall. Beta-1,3D-glucans is a substance that is extracted from red yeast, and the "1,3" terminology indicates that the substance is soluble and flexible.

One study has suggested that beta-D-glucans can have revitalizing effects on aging skin. Among 150 female volunteers aged 35-60, those given a cosmetic preparation containing yeast beta-glucans were said to have significantly reduced number, depth, and length of wrinkles when compared to controls. The elasticity of the skin was also improved. For these reasons, beta-1,3D-glucans may be advantageously included in the embodiments described in Tables I and II.

In the topical compositions according to Tables I and II, zinc gluconate has been exploited for its outstanding role in the formation of "zinc fingers." A zinc finger is a structure which is 30 amino acids long and is tightly bound with an atom of zinc. Zinc fingers are known for their beneficial interaction with DNA to regulate the activity of genes. Furthermore, it has long been recognized that zinc is capable of maintaining the integrity of biological membranes by protecting them against oxidative injury. The element zinc also supports the synthesis and formation of the copper chaperone metallothionein.

For the above reasons, zinc gluconate is advantageously included in the embodiments described in Tables I and II. In alternative embodiments of the invention, other substances that encourage the formation of different copper chaperones may be used in place of, or in addition to, zinc gluconate.

As indicated in Tables I and II, topical compositions for accelerated production of collagen proteins according to embodiments of the invention further include silicon (colloidal silicic acid). In the preferred composition described in Table II, the colloidal silicic acid amounts to about 0.02% m/v of the composition.

Silicon is required for the enzyme prolylhydroxylase, which participates in the formation of connective tissue and skin. The enzyme also appears to be involved in the synthesis of both glycosaminoglycan and collagen. Since most of the silicon in the body is found in the connective tissue and not bound to plasma, evidence suggests its role in the participation of skin development to be favorable.

Studies have shown that women who apply silicic acid to their faces twice daily show statistically significant improvements in both thickness and strength of the skin, and improvements in the diminishment of wrinkles was also noted. For these reasons, silicon is advantageously included in the embodiments described in Tables I and II.

A person skilled in the art will be able to practice the invention in view of the present description, where numerous details have been set forth in order to provide a more thorough understanding of the invention. In other instances, well-known features have not been described in detail in order not to unnecessarily obscure the invention.

For example, the embodiments listed in Table I express a preferred minimum concentration limit for the solutes listed in the Table. However, it should be emphasized that even trace amounts of the solutes listed in Table I may achieve some of the beneficial effects described above, albeit much less dramatically.

Thus, some embodiments of the invention may include one or more of the solutes listed in Table I, but at a concentration that is much less than the preferred minimum concentration limit expressed in Table I.

Similarly, the embodiments described in Table I express a preferred maximum concentration limit for the solutes listed in the Table. Typically, there is some upper bound where a law of diminishing returns seems to operate. That is, there typically exists an upper concentration limit, where increasing the concentration of a substance any further beyond that limit becomes potentially unsafe and/or surpasses the capability of the body or other reactants in the composition to effectively utilize the substance.

Thus, some other embodiments of the invention may include one or more of the solutes listed in Table II, but at a concentration that is greater than the preferred maximum concentration limit expressed in Table I.

As such, it should be recognized that the concentration ranges given in Table I represent preferred ranges where each of the solutes may achieve optimal results, and that the preferred ranges do not strictly limit the concentration of solutes in embodiments of the invention to the specified ranges. Likewise, the particular concentrations given in Table II represent a preferred formulation within the preferred ranges of Table I.

The invention may additionally be practiced in many different ways. For example, the act of preparing a composition according to Tables I or II above are considered to be embodiments of the invention, as is the act of applying the compositions prepared according to Tables I or II above to the skin of an animal to encourage the accelerated productions of collagen proteins.

Similarly, it is anticipated that the solutes listed in Table I or Table II may be mixed together in the appropriate proportions prior to being added to a predetermined amount of solvent, that the individual solutes may be sequentially added to the solvent, or that the solutes may be added to the solvent using some combination of the two processes.

Likewise, mixtures of solutes or separately packaged solutes according to Table I or Table II that are pre-measured and ready for introduction into a predetermined amount of solvent are considered to be compositions according to embodiments of the invention.

It should be appreciated that reference throughout this specification to "one embodiment" or "an embodiment" means that a particular feature, structure or characteristic described in connection with the embodiment is included in at least one embodiment of the invention. Therefore, it should be emphasized and appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Similarly, it should be appreciated that in the foregoing description of exemplary embodiments of the invention, various features of the invention are sometimes grouped together in a single embodiment, figure, or description thereof for the purpose of streamlining the disclosure aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects may lie in less than all features of a single disclosed embodiment. Thus, the claims following this detailed description are hereby expressly incorporated into this detailed description, with each claim standing on its own as a separate embodiment of this invention.

Having described and illustrated the inventive aspects by describing and explaining several preferred embodiments of the invention, it should be apparent that the embodiments may be modified in arrangement and detail without departing from such principles.

I claim all modifications and variation coming within the spirit and scope of the attached claims:

1. A liquid solution for topical application to the skin of an animal, the liquid solution consisting of solutes and a solvent, the solutes comprising:
   ascorbate;
   tropocollagen factors including L-proline, glycine and L-lysine; and
   zinc gluconate,
   wherein the liquid solution contains the solutes in amounts effective to accelerate the production of collagen proteins within an animal when applied to the skin of the animal.

2. The liquid solution of claim 1,
   wherein the ascorbate is about 15 to about 30% m/v of the liquid solution.

3. The liquid solution of claim 2, wherein the ascorbate is about 21.5% m/v of the liquid solution.

4. The liquid solution of claim 3, wherein the tropocollagen factors are about 4.5 to about 12.0% m/v of the liquid solution.

5. The liquid solution of claim 4, wherein the tropocollagen factors are about 8.0% m/v of the liquid solution.

6. The liquid solution of claim 5, wherein the copper is about 0.5 to about 5.0% m/v of the liquid solution.

7. The liquid solution of claim 6, wherein the copper is about 1.0% m/v of the liquid solution.

8. The liquid solution of claim 7, wherein the zinc gluconate is about 0.01 to about 0.03% m/v of the liquid solution.

9. The liquid solution of claim 8, wherein the zinc gluconate is about 0.021% m/v of the liquid solution.

10. The liquid solution of claim 9, the solutes further comprising bioflavonoids, wherein the bioflavonoids are about 0.5 to about 1.5% m/v of the liquid solution.

11. The liquid solution of claim 10, wherein the bioflavonoids are about 1.0% m/v of the liquid solution.

12. The liquid solution of claim 11, the solutes further comprising silicon, wherein the silicon is about 0.01 to about 0.03% m/v of the liquid solution.

13. The liquid solution of claim 12, wherein the silicon is about 0.02% m/v of the liquid solution.

14. The liquid solution of claim 1, in which the solutes do not comprise collagen.

15. The liquid solution of claim 1, wherein the glycine is 2 to 5% m/v of the liquid solution, the L-proline is 2 to 5% m/v of the liquid solution, and the L-lysine is 0.5 to 2% m/v of the liquid solution.

16. The liquid solution of claim 15, wherein the glycine is about 3.33% m/v of the liquid solution, the L-proline is about 3.33% m/v of the liquid solution, and the L-lysine is about 1.31% m/v of the liquid solution.

17. The liquid solution of claim 1, wherein the glycine constitutes about 41.67 to about 44.44% of the tropocollagen factors, the L-proline constitutes about 41.67 to about 44.44% of the tropocollagen factors, and the L-lysine constitutes about 11.11 to about 16.67% of the tropocollagen factors.

18. The liquid solution of claim 17, wherein the glycine constitutes about 42% of the tropocollagen factors, the L-proline constitutes about 42% of the tropocollagen factors, and the L-lysine constitutes about 16% of the tropocollagen factors.

19. A liquid solution for topical application to the skin of an animal, the liquid solution comprising:
   ascorbate;
   tropocollagen factors including L-proline, glycine and L-lysine;
   beta, 3D-glucans;
   bioflavonoids;
   silicon;
   copper;
   and zinc gluconate.

20. The liquid solution of claim 19, wherein the beta-1,3D-glucans are about 0.05 to about 0.15% m/v of the liquid solution.

21. The liquid solution of claim 19, wherein the bioflavonoids are about 0.5 to about 1.5% m/v of the liquid solution.

22. The liquid solution of claim 19, in which a ratio between copper and an amount of zinc found in the zinc gluconate is about 16:1 to about 500:1.

23. The liquid solution of claim 19, in which the solutes do not comprise collagen.

24. The liquid solution of claim 1, wherein the solvent comprises an alcohol solution.

25. A topical skin care composition, comprising:
   solutes comprising ascorbate, bioflavonoids, copper, zinc gluconate and tropocollagen factors including L-proline, glycine and L-lysine; and
   a solvents,
   wherein the composition contains the solutes in amounts effective to accelerate the production of collagen proteins within an animal when applied to the skin of the animal.

* * * * *

UNITED STATES PATENT AND TRADEMARK OFFICE
CERTIFICATE OF CORRECTION

PATENT NO.        : 7,700,083 B2                                                Page 1 of 1
APPLICATION NO.   : 11/462347
DATED             : April 20, 2010
INVENTOR(S)       : Kevin Meehan It is certified that error appears in the above-identified patent and that said Letters Patent is hereby corrected as shown below:

Column 5, lines 59-60, between the paragraph ending "... in Tables I and II." and the paragraph beginning "In the topical . . .", insert the following paragraph -- As indicated in Tables I and II, topical compositions for accelerated production of collagen proteins according to embodiments of the invention further include zinc gluconate, which provides zinc. In the preffered composition described in Table II, the zinc gluconate totals about 0.021 % m/v of the composition. --;
      Column 7, lines 49, the word "L-lysine;" should read -- L-lysine; copper; --;
      Column 8, line 8, the words "wherein the" should read -- the --;
      Column 8, line 40, the word "beta, 3D-glucans" should read -- beta-1,3D-glucans --;
      Column 8, line 60, the word "solvents" should read -- solvent --.

Signed and Sealed this
Twenty-fifth Day of January, 2011

David J. Kappos
*Director of the United States Patent and Trademark Office*